(12) United States Patent
Ludwig

(10) Patent No.: US 8,885,035 B2
(45) Date of Patent: Nov. 11, 2014

(54) ELECTRONIC IMAGING FLOW-MICROSCOPE FOR ENVIRONMENTAL REMOTE SENSING, BIOREACTOR PROCESS MONITORING, AND OPTICAL MICROSCOPIC TOMOGRAPHY

(75) Inventor: Lester F. Ludwig, Belmont, CA (US)

(73) Assignee: Lester F. Ludwig, San Antonio, TX (US)

( * ) Notice: Subject to any disclaimer, the term of this patent is extended or adjusted under 35 U.S.C. 154(b) by 754 days.

(21) Appl. No.: 12/817,107

(22) Filed: Jun. 16, 2010

(65) Prior Publication Data

US 2010/0315501 A1    Dec. 16, 2010

Related U.S. Application Data

(60) Provisional application No. 61/268,900, filed on Jun. 16, 2009.

(51) Int. Cl.
*H04N 7/18* (2006.01)
*G01N 15/14* (2006.01)

(52) U.S. Cl.
CPC .................................. *G01N 15/1475* (2013.01)
USPC .......................................................... 348/79

(58) Field of Classification Search
USPC .......................................................... 384/79
See application file for complete search history.

(56) References Cited

U.S. PATENT DOCUMENTS

| 4,015,366 | A | * | 4/1977 | Hall, III ........................ 47/1.43 |
|---|---|---|---|---|
| 4,165,532 | A | * | 8/1979 | Kendall et al. ................ 700/284 |
| 4,538,299 | A | * | 8/1985 | DeForest ....................... 382/197 |
| 4,804,267 | A | * | 2/1989 | Greenfield ..................... 356/335 |
| 4,833,382 | A | * | 5/1989 | Gibbs ............................ 318/640 |
| 5,101,978 | A | * | 4/1992 | Marcus .......................... 209/3.1 |
| 5,471,294 | A | * | 11/1995 | Ogino ............................ 356/73 |
| 5,736,404 | A | * | 4/1998 | Yassinzadeh et al. .......... 436/52 |
| 5,848,177 | A | * | 12/1998 | Bauer et al. ................... 382/128 |
| 5,983,120 | A | * | 11/1999 | Groner et al. ................. 600/310 |
| 6,115,119 | A | * | 9/2000 | Sieracki et al. ............... 356/337 |
| 6,184,978 | B1 | * | 2/2001 | Kasdan et al. ................ 356/246 |
| 6,424,415 | B1 | * | 7/2002 | Kasdan et al. ................ 356/246 |
| 6,924,149 | B2 | * | 8/2005 | Turner et al. .................. 436/148 |
| 7,161,674 | B2 | * | 1/2007 | Gold et al. ..................... 356/338 |
| 7,442,339 | B2 | * | 10/2008 | Sundararajan et al. .... 422/82.05 |
| 7,702,172 | B2 | * | 4/2010 | Chapoulaud .................. 382/256 |
| 2004/0109386 | A1 | * | 6/2004 | Gold et al. ..................... 366/336 |
| 2004/0136593 | A1 | * | 7/2004 | Chapoulaud .................. 382/199 |
| 2005/0110725 | A1 | * | 5/2005 | Kwak et al. .................... 345/76 |

(Continued)

*Primary Examiner* — Dave Czekaj
*Assistant Examiner* — Kehinde O Abimbola
(74) *Attorney, Agent, or Firm* — Procopio, Cory, Hargreaves & Savitch LLP

(57) ABSTRACT

An electronic imaging flow-microscope for remote environmental sensing, bioreactor process monitoring, and optical microscopic tomography applications is described. A fluid conduit has a port on each end of a thin flat transparent fluid transport region. A planar illumination surface contacts one flat side of the transparent fluid transport region and a planar image sensing surface contacts the other flat side. Light from the illumination surface travels through the transparent fluid transport region to the planar image sensing surface, producing a light field affected by the fluid and objects present. The planar image sensing surface creates electrical image signals responsive to the light field. The planar illumination surface can be light emitting elements such as LEDs, OLEDs, or OLET, whose illumination can be sequenced in an image formation process. The flow microscope can further comprise flow-restricting valves, pumps, energy harvesting arrangements, and power management.

20 Claims, 20 Drawing Sheets

(56) References Cited

U.S. PATENT DOCUMENTS

2005/0260553 A1* 11/2005 Berzin ............................ 435/3
2006/0184037 A1* 8/2006 Ince et al. .................... 600/476
2006/0186899 A1* 8/2006 Gold et al. ................... 324/665
2010/0316292 A1* 12/2010 O'Hara et al. ................ 382/168
2010/0328660 A1* 12/2010 Hager .......................... 356/326
2011/0027824 A1* 2/2011 Turner et al. .................... 435/39
2012/0127298 A1* 5/2012 Sieracki et al. ................. 348/79

* cited by examiner

| | pixels / sq.mm | mm/px | µm/px | # pixels | Amoeba - 700µm | Amoeba - 1000µm | sensor area size (sq.mm) |
|---|---|---|---|---|---|---|---|
| Andanta Ultra-High Res CCD | 4933 | 0.00020272 | 0.2027164 | 111000000 | 3453.1 | 4933 | 22500 |
| Megaplus ER 11000 (lower) | 12732 | 7.8542E-05 | 0.07854226 | 11000000 | 8912.4 | 12732 | 864 |
| Megaplus ER 11000 (upper) | 111111 | 9E-06 | 0.00900001 | 96000000 | 77777.7 | 111111 | 864 |
| Kodak KAI-11002 | 12458 | 8.027E-05 | 0.08026971 | 11100000 | 8720.6 | 12458 | 891 |
| DCU 223 M/C Sony | 10971 | 9.1149E-05 | 0.09114939 | 786432 | 7679.7 | 10971 | 71.68 |
| DCU 224 M/C Sony | 8126 | 0.00012306 | 0.12306178 | 1310720 | 5688.2 | 8126 | 161.28 |
| Kodak KAI-08050 | 33653 | 2.9715E-05 | 0.02971503 | 8147712 | 23557.1 | 33653 | 242.11 |

Figure 12a

| | pixels / sq.mm | mm/px | µm/px | # pixels | Protozoa (type A) - 10µm | Protozoa (type B) - 50µm | Protozoa (type C) - 1000µm | sensor area size (sq.mm) |
|---|---|---|---|---|---|---|---|---|
| Andanta Ultra-High Res CCD | 4933 | 0.00020272 | 0.2027164 | 111000000 | 49.33 | 246.65 | 4933 | 22500 |
| Megaplus ER 11000 (lower) | 12732 | 7.8542E-05 | 0.07854226 | 11000000 | 127.32 | 636.6 | 12732 | 864 |
| Megaplus ER 11000 (upper) | 111111 | 9E-06 | 0.00900001 | 96000000 | 1111.11 | 5555.55 | 111111 | 864 |
| Kodak KAI-11002 | 12458 | 8.027E-05 | 0.08026971 | 11100000 | 124.58 | 622.9 | 12458 | 891 |
| DCU 223 M/C Sony | 10971 | 9.1149E-05 | 0.09114939 | 786432 | 109.71 | 548.55 | 10971 | 71.68 |
| DCU 224 M/C Sony | 8126 | 0.00012306 | 0.12306178 | 1310720 | 81.26 | 406.3 | 8126 | 161.28 |
| Kodak KAI-08050 | 33653 | 2.9715E-05 | 0.02971503 | 8147712 | 336.53 | 1682.65 | 33653 | 242.11 |

Figure 12b

| | pixels / sq.mm | mm/px | µm/px | # pixels | Rotifiers (type A) - 100µm | Rotifiers (type A) - 500µm | Rotifiers (type B) - 50µm | Rotifiers (type B) - 2000µm | sensor area size (sq.mm) |
|---|---|---|---|---|---|---|---|---|---|
| Andanta Ultra-High Res CCD | 4933 | 0.00020272 | 0.2027164 | 111000000 | 493.3 | 2466.5 | 246.65 | 9866 | 22500 |
| Megaplus ER 11000 (lower) | 12732 | 7.8542E-05 | 0.07854226 | 11000000 | 1273.2 | 6366 | 636.6 | 25464 | 864 |
| Megaplus ER 11000 (upper) | 111111 | 9E-06 | 0.00900001 | 96000000 | 11111.1 | 55555.5 | 5555.55 | 222222 | 864 |
| Kodak KAI-11002 | 12458 | 8.027E-05 | 0.08026971 | 11100000 | 1245.8 | 6229 | 622.9 | 24916 | 891 |
| DCU 223 M/C Sony | 10971 | 9.1149E-05 | 0.09114939 | 786432 | 1097.1 | 5485.5 | 548.55 | 21942 | 71.68 |
| DCU 224 M/C Sony | 8126 | 0.00012306 | 0.12306178 | 1310720 | 812.6 | 4063 | 406.3 | 16252 | 161.28 |
| Kodak KAI-08050 | 33653 | 2.9715E-05 | 0.02971503 | 8147712 | 3365.3 | 16826.5 | 1682.65 | 67306 | 242.11 |

Figure 12c

| | pixels / sq.mm | mm/px | µm/px | # pixels | Amoeba - 700µm | Amoeba - 1000µm |
|---|---|---|---|---|---|---|
| Canon D30, 3MP | 95.4 | 0.0104822 | 10.48218 | 3000000 | 66.78 | 95.4 |
| Nikon Coolpix 995, 3MP | 290 | 0.0034483 | 3.4482759 | 3000000 | 203 | 290 |
| Minolta Xi, 3MP | 384 | 0.0026042 | 2.6041667 | 3000000 | 268.8 | 384 |
| OmniVision OV5620, 5MP | | | 2.2 | 5000000 | 318.1818 | 454.5455 |
| OmniVision OV5630/5633, 5MP | | | 1.75 | 5000000 | 400 | 571.4286 |
| OmniVision OV8810/8812, 8MP | | | 1.4 | 8000000 | 500 | 714.2857 |

Figure 13

ELECTRONIC IMAGING FLOW-MICROSCOPE FOR ENVIRONMENTAL REMOTE SENSING, BIOREACTOR PROCESS MONITORING, AND OPTICAL MICROSCOPIC TOMOGRAPHY

CROSS-REFERENCE TO RELATED APPLICATIONS

This application claims benefit of priority of U.S. provisional application Ser. No. 61/268,900 filed on Jun. 16, 2009, incorporated herein by reference.

BACKGROUND OF THE INVENTION

1. Field of the Invention

The present invention generally relates to electronic cameras electronic imaging, fluid flow microscopes, and image processing, and in particular to how these may be combined in various ways to create a small low-power inexpensive flow microscope element for applications in environmental remote telemetry sensing, bioreactor monitoring, and other applications.

2. Background

Powerful new sensor capabilities and telemetry costs are radically evolving and have been integrated into environmental and contamination monitoring systems and Geographic Information Systems (GIS) as described in related U.S. patent application Ser. No. 12/817,074 filed on Jun. 16, 2010. Still-image, video, and audio field sensors can provide very useful environmental information as argued therein. Among the more useful possible applications for still-image and video is an inexpensive submersible flow microscope that can be used to visually monitor micro-organism and other microscopic affairs in flowing or standing surface water (among other uses). Such a flow microscope would need to be physically small, sturdy, low-energy consuming, easy to use, inexpensive, and remotely controllable by electrical or data signals. Once crafted, the resulting technology can be used as a laboratory instrument, for example as can be used in conjunction with a bioreactor.

To facilitate the above goals, a number of technology developments and particulars of possible flow microscope optical arrangements can be leveraged. In particular, image sensing elements are decreasing in cost as they increase in resolution and decrease in sensor array area size. These trends, together with the small size of objects to be viewed (assuming the incoming fluid is adequately clear of pre-filtered) permit a (2-dimensional) "contact imaging" approach, not unlike the 1-dimensional scanning bar arrangements employed in contemporary fax machines. Additional technology additions provide a wider range of performance, features, and capabilities, including opportunities for optical microscopic tomography. Additional advancements in power management electronics and image processing facilitate support other aforementioned needs of a flow microscope for environmental monitoring applications.

SUMMARY OF THE INVENTION

The invention comprises a fluid conduit comprising a port on each end of a thin flat transparent fluid transport region. The transparent fluid transport region comprises two parallel flat sides. A planar illumination surface is in contact with one of the flat sides; and a planar image sensing surface is in contact with the other flat side for receiving light fields and responsively creating electrical image signals. The light from the planar illumination surface travels into the transparent fluid transport region and produces a resulting light field affected by the fluid and any organisms or objects in the fluid. The resulting light field is presented to the planar image sensing surface, and the planar image sensing surface creates electrical image signals responsive to the resulting light field.

Various aspects of the invention may include a funnel port to capture water for environmental monitoring, an screen attached or adjacent to the funnel to filter out water-borne debris, and one or more electric knife valve(s) for trapping fluids for a fixed view or for removing debris at fluid constrictions. One or more pumps may be incorporated to facilitate desired fluid flow or to clear blockages or debris from the system.

The inventive system may also include power management electronics wherein electrical power is generated by fluid flow.

Electric illumination provides a light source from the bottom and a video and/or imaging sensor is positioned on the opposite side of a transparent flat fluidic passageway. The imaging sensor captures the images of particles of microscopic organisms that are suspended in the water. The imaging sensor can be implemented (with or without lenses) in a 2-dimensional manner similar to the 1-dimensional imaging arrangements of a document scanner. The source of illumination may be a light-emitting array. The planar illumination surface may be individual light-emitting pixels wherein the individual light-emitting pixels can be sequenced.

The light-emitting array may provide sequenced spatially modulated illumination, the sequence operated as part of the imaging system producing a fully-formed image output. The array may produce a partially-formed image output that can be subsequent processed by another processor to produce a fully-formed image output.

The invention provides data that can be used for optical tomography or used to produce tomography output.

BRIEF DESCRIPTION OF THE DRAWINGS

The above and other aspects, features, and advantages of the present invention will become more apparent upon consideration of the following description of preferred embodiments, taken in conjunction with the accompanying drawing figures.

FIG. 2b depicts an adaptation of the exemplary embodiment of FIG. 1c further comprising an internal pump servicing the opposite port than the adaptation of FIG. 2a.

FIG. 4b depicts flow in one direction through the exemplary fitting and housing arrangement of FIG. 4a.

FIG. 4c depicts flow in the opposite direction as that for FIG. 4b through the exemplary fitting and housing arrangement of FIG. 4a.

FIG. 12a is a table comparing attributes example contemporary high-resolution optical image-sensing element products to the width of example Amoeba sizes.

FIG. 12b is a table comparing attributes example contemporary high-resolution optical image-sensing element products to the width of example Protozoa sizes.

FIG. 12c is a table comparing attributes example contemporary high-resolution optical image-sensing element products to the width of example Rotifer sizes.

FIG. 13 is a table comparing attributes example contemporary miniature inexpensive cell-phone camera image-sensing element products to the width of example Amoeba sizes.

FIG. 14b depicts the exemplary single-cell organism in comparison an exemplary image sensor pixel array spacing of twice the resolution of that in FIG. 14a.

FIG. 14c depicts the exemplary single-cell organism in comparison an exemplary image sensor pixel array spacing of four times the resolution of that in FIG. 14a.

DETAILED DESCRIPTION

In the following detailed description, reference is made to the accompanying drawing figures which form a part hereof, and which show by way of illustration specific embodiments of the invention. It is to be understood by those of ordinary skill in this technological field that other embodiments can be utilized, and structural, electrical, as well as procedural changes can be made without departing from the scope of the present invention. Wherever possible, the same element reference numbers will be used throughout the drawings to refer to the same or similar parts.

The present invention is an electronic imaging flow-microscope for use in applications such as environmental remote telemetry sensing and bioreactor process monitoring. The invention can also be used in a wide range of other applications, such as monitoring in manufacturing processes or monitoring body fluids in medical applications.

Figure 1A:
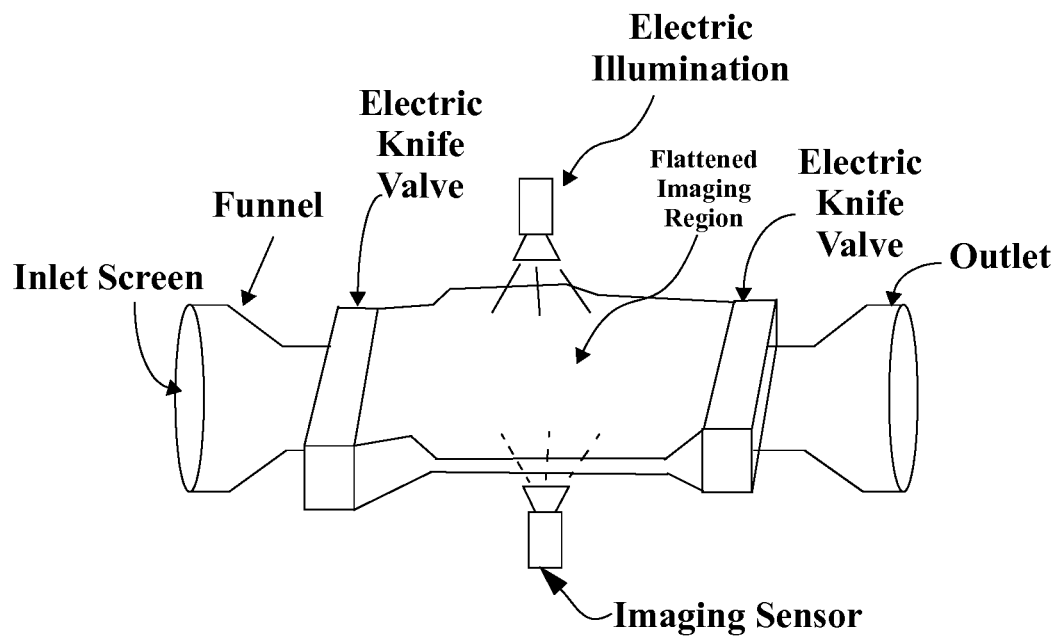
FIG. 1a depicts an exemplary embodiment of the invention with exemplary features for environmental remote telemetry sensing applications.

FIG. 1a depicts the invention with features for environmental remote telemetry sensing applications. For environmental monitoring, monitored water can flow into the funnel. In some applications, a screen attached within or adjacent to the funnel can filter out debris in the water. Electric illumination provides light source from the bottom and a video and/or imaging sensor on the opposite side of a transparent flat fluidic passageway captures the images of particles of microscopic organisms that are suspended in the water. In some applications, the imaging sensor can be implemented (without lenses) in a 2-dimensional manner similar to the 1-dimensional imaging arrangements of a document scanner. The imaging sensor may include a light-emitting array as the source of illumination providing sequenced spatially modulated illumination, the sequence operated as part of the imaging system. This arrangement produces a fully-formed image output. The arrangement may also produce a partially-formed image output that can be subsequent processed by another processor to produce a fully-formed image output. The arrangement also can be used to produce tomography output. The imaging sensor also can have magnifying lenses.

One or more electric knife valve(s) may be operated to trap fluids for a fixed view. The knife valves may be designed in conjunction with the filters so as to not create a situation wherein small water organisms are injured. In some applications, the electric knife valve(s) can be operated in such a manner as to remove debris at fluid constrictions.

Figure 1B:
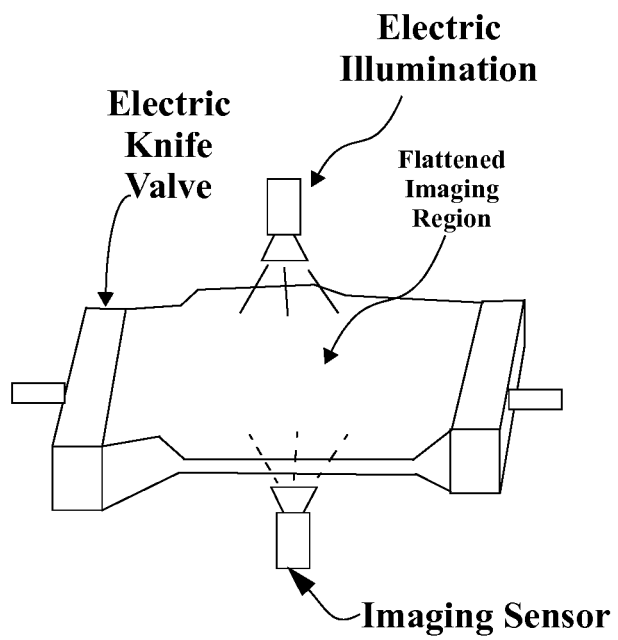
FIG. 1b depicts an exemplary embodiment of the invention with exemplary features for bioreactor monitoring applications.

FIG. 1b depicts exemplary features for applications such as bioreactor process monitoring, manufacturing process monitoring, monitoring of body fluids in medical applications, etc. In such applications the funnel, screen, and/or valves may be replaced with tubing ports, size filters, or other elements and/or arrangements as advantageous for the application.

Figure 1C:
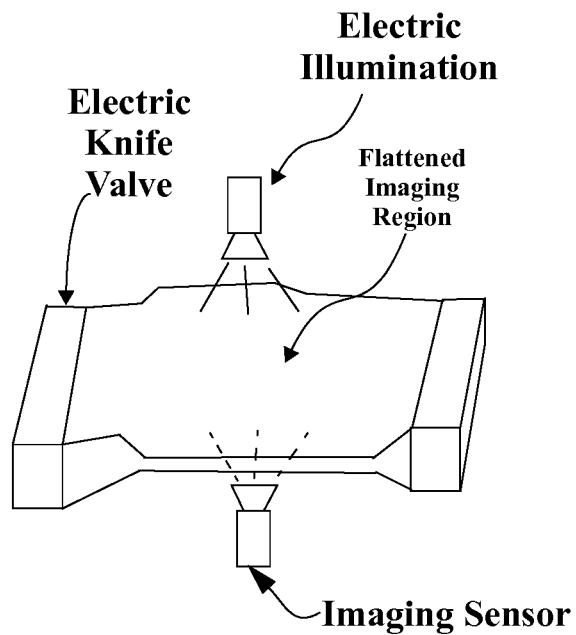
FIG. 1c depicts a generic form of an exemplary embodiment of the invention that can be augmented with different types of external flow fittings on the ports of the device so as to selectively form the exemplary embodiments of FIG. 1a and FIG. 1b as well as other configurations arrangements.

FIG. 1c depicts a generic form of the invention that can be augmented with different types of external flow fittings on the ports of the device so as to selectively form the embodiments of FIG. 1a and FIG. 1b as well as other configurations arrangements.

In one arrangement, the invention can comprise a fluid conduit comprising a port on each end and a thin flat transparent fluid transport region between the ports, the transparent fluid transport region comprising two parallel flat sides; a planar illumination surface in contact with one of the flat sides of the transparent fluid transport region; and a planar image sensing surface in contact with the other of the flat sides of the transparent fluid transport region for receiving light fields and responsively creating electrical image signals.

In such an arrangement, light from the planar illumination surface travels into the transparent fluid transport region, producing a resulting light field affected by the fluid and any microscopic organisms and/or microscopic objects in the fluid, the resulting light field is presented to the planar image sensing surface, and the planar image sensing surface creates electrical image signals responsive to the resulting light field.

Figure 2A:
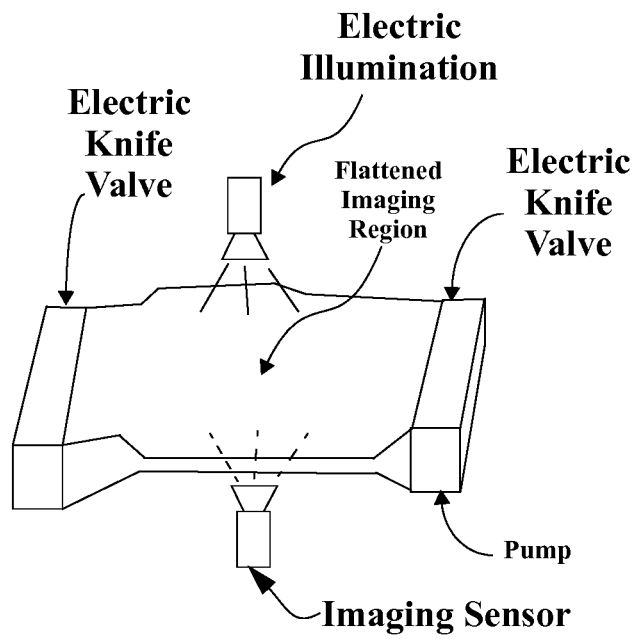
FIG. 2a depicts an adaptation of the exemplary embodiment of FIG. 1c further comprising an internal pump servicing one port.
Figure 2B:
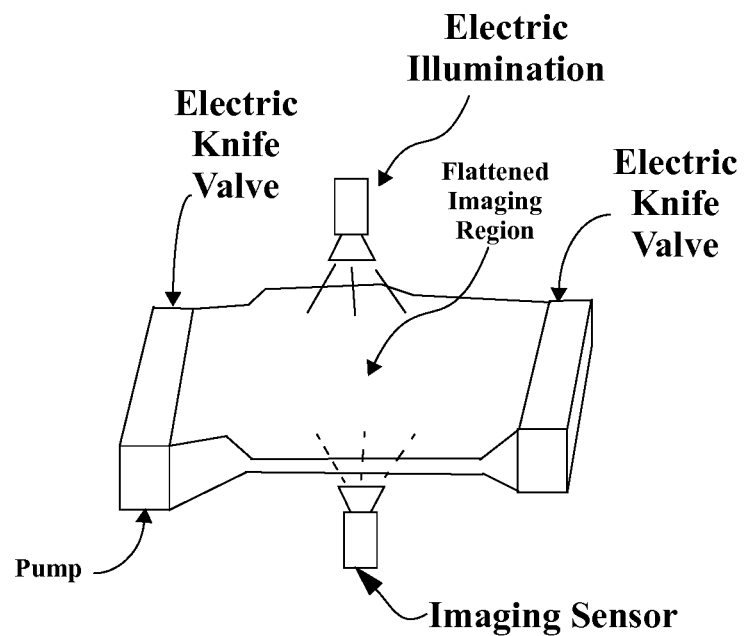
Figure 2C:
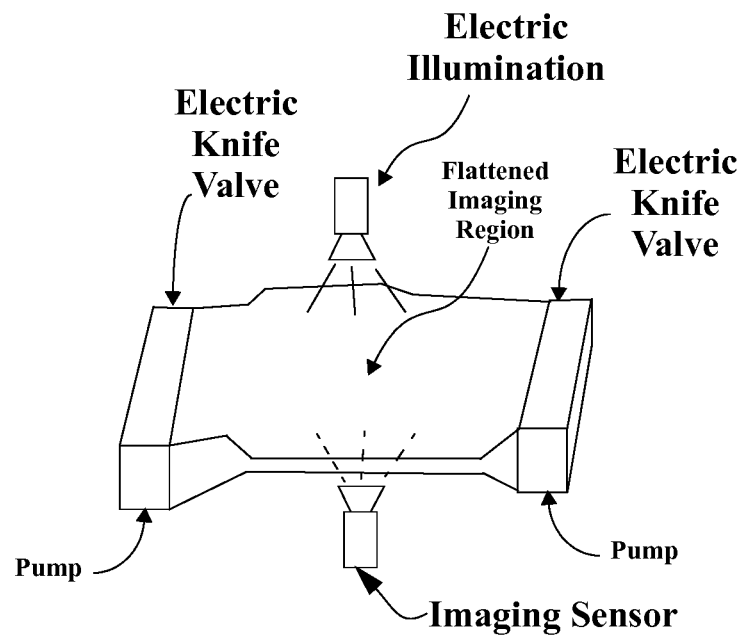
FIG. 2c depicts an adaptation of the exemplary embodiment of FIG. 1c further comprising two internal pumps, one to service each port.

In some situations, the water or fluid to flow through the flow microscope has enough inherent pressure to flow through the flow microscope at an adequate pace. In some situations, the inherent pressure may be too high and the invention can operate the electric knife valves to restrict the flow rate. In other situations, there may be inadequate inherent pressure or contrary-direction inherent pressure. In such situations, the invention can be further provided with one or more internal fluid pump(s). The pump(s) can be unidirectional. In other implementations, the pump(s) can be bidirectional. The pump(s) can be a diaphragm pump, a rotating vane or turbine pump. When the pump(s) are a rotating vane or turbine pump, the pump may also be used in a passive unpowered mode to generate an electrical signal responsive to rotation of the rotating vane or turbine. The electrical signal also can be used for flow-rate measurements. FIG. 2a depicts an adaptation of FIG. 1c further comprising an internal pump servicing one port. FIG. 2b depicts an adaptation of FIG. 1c having an internal pump servicing the opposite port than the adaptation of FIG. 2a. FIG. 2c depicts an adaptation of FIG. 1c further comprising two internal pumps, one to service each port. In a variation of the arrangement depicted in FIG. 2c, one of the pump elements can be used as a pump and the other used as a flowmeter. In a further adaptation of this, one of the pumps can be replaced with flowmeter. When employing one or more pumps, the pumps can be, preventatively or as needed, be operated in pulsed and/or direction-reversing modes to prevent clogs, or clear accumulated debris, etc.

Exemplary Embodiments for Environmental Monitoring Applications

The invention can be used as a component in an environmental monitoring system or environmental GIS system as described in related U.S. patent application Ser. No. 12/817,074 filed on Jun. 16, 2010. For such applications, the invention can advantageously further internally comprise other types of sensors such as an oxygen sensor, pH sensor, temperature sensor, specialized ion sensor, affinity sensor, biomolecule sensor, etc.

Figure 3:
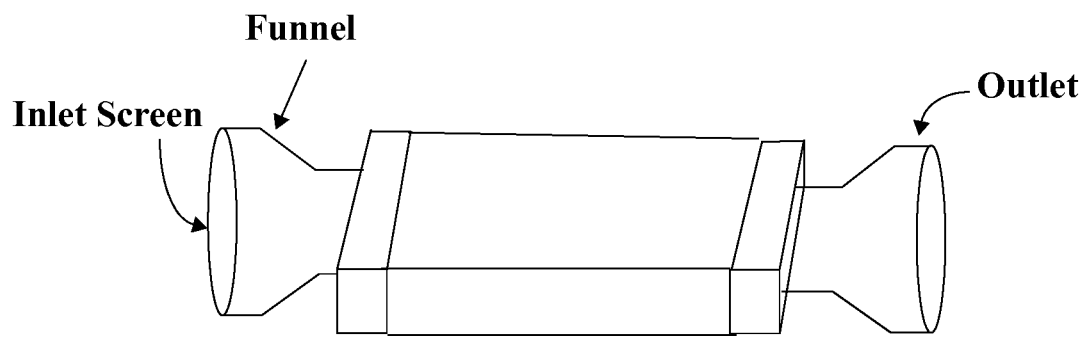
FIG. 3 depicts an exemplary housing arrangement for the exemplary embodiment of FIG. 1a, designed for flow in one direction.
Figure 4A:
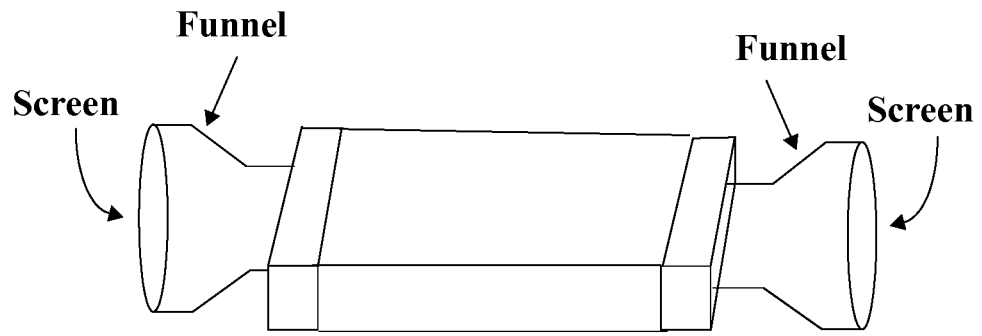
FIG. 4a depicts an exemplary fitting and housing arrangement as may be used in conjunction with the exemplary embodiments of FIGS. 2a-2c, designed for flow in both directions.
Figure 4B:
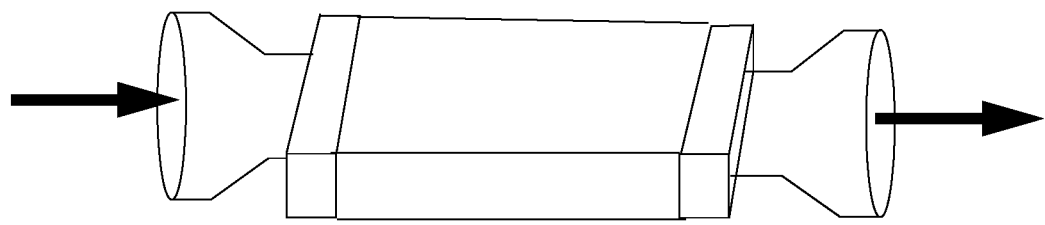
Figure 4C:
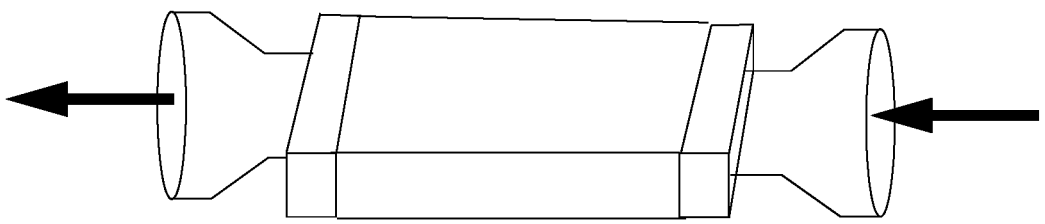
Figure 5A:
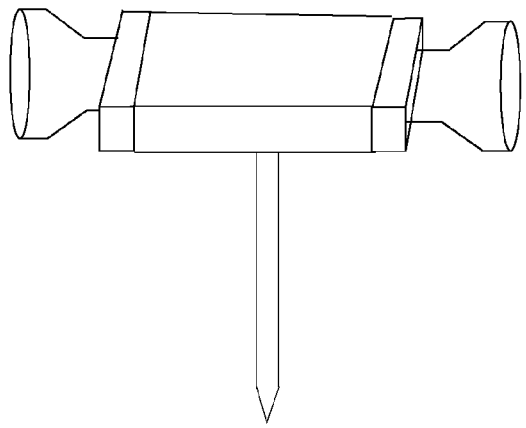
FIGS. 5a-5d depicts various exemplary staking arrangements for example as can be used to secure a flow camera in a flowing waterway or standing body of water.
Figure 5B:
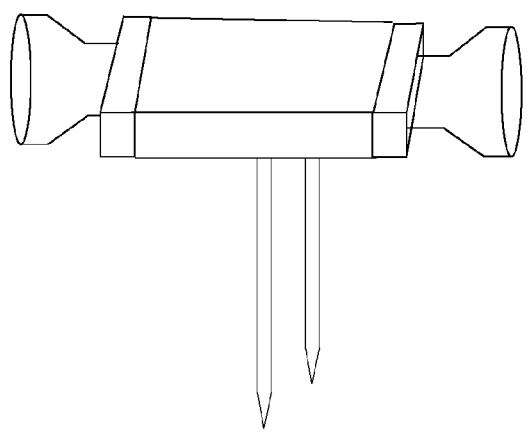
Figure 5C:
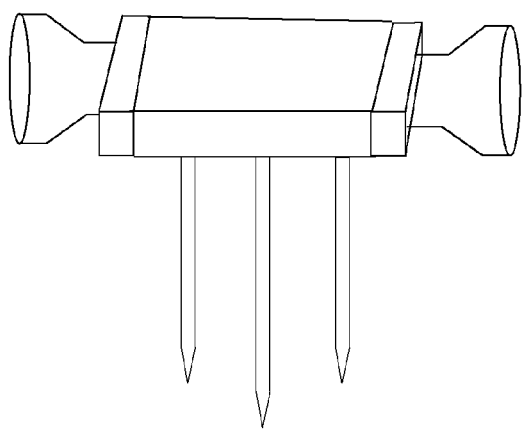
Figure 5D:
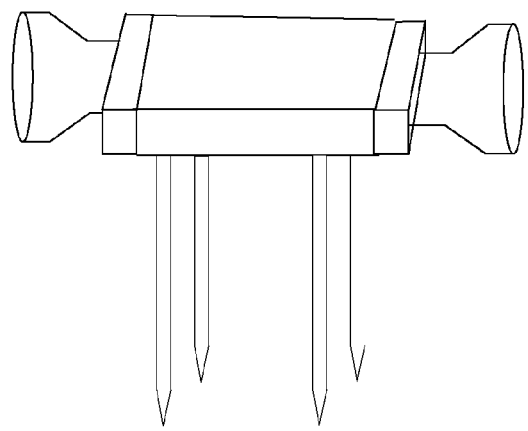

FIG. 3 depicts a housing arrangement of FIG. 1a, designed for flow in one direction. As another example, FIG. 4a depicts an fitting and housing arrangement as may be used in conjunction with FIGS. 2a-2c, designed for flow in both directions. Accordingly, FIG. 4b depicts flow in one direction through the fitting and housing arrangement of FIG. 4a, while FIG. 4c depicts flow in the opposite direction.

The invention may be deployed in flowing waterways (rivers, stream, brooks, tidal paths, estuaries, etc.), standing bodies of water (lakes, bays, shoreline coastal water, bogs, sloughs, swamps, etc.), or other volumes of moving, standing, or occasional water (underground water wells, urban piping, storm sewers, drainage ditches, levy areas, etc.). The invention in these cases is typically submerged when in operation (at least part of the time) and in most implementations may be provided with an electrical cable for signals In some deployments of the invention, the flow microscope preferably will be secured at a fixed location at a fixed distance from the water floor or shoring. In wild areas, the invention may be secured by stakes that can be pushed, hammered, or screwed into the ground. FIGS. 5a-5d depicts various exemplary staking geometry arrangements for example as can be used to secure a flow camera in a flowing waterway or standing body of water.

Figure 6:
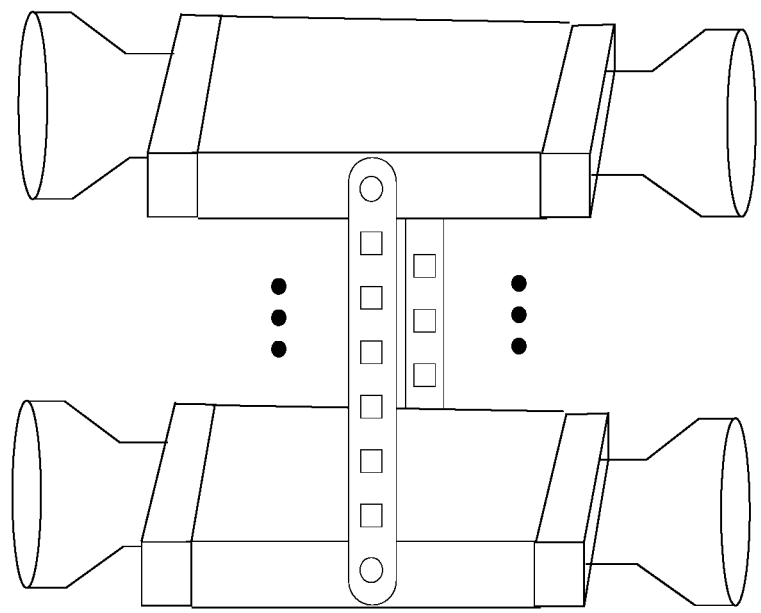
FIG. 6 depicts an exemplary aligned ganging arrangement as for example can be used to secure a group of flow camera in a surface waterway or body of water.
Figure 7:
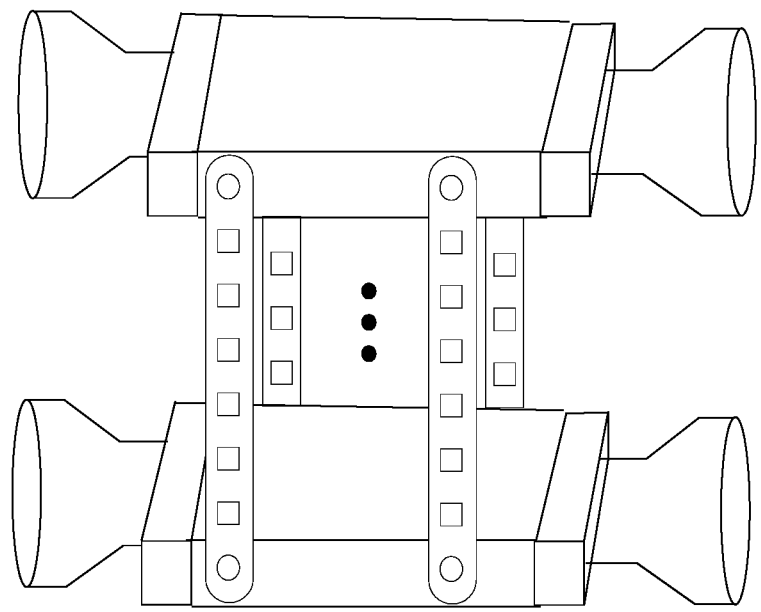
FIG. 7 depicts another exemplary aligned ganging arrangement providing more alignment stability that the arrangement of FIG. 6.

In some deployments of the invention, a plurality of flow microscopes will preferably be co-deployed in the same immediate location. For example, water may be sampled at various heights from the water floor, or various distances from the water shoring. FIG. 6 depicts an aligned ganging arrangement that can secure a group of flow cameras in a surface waterway or body of water. Here, any of a number of types and/or combinations of keyed holes (here depicted as squares), extrusions, mounting ears, aligning pins, keyed fasteners, etc. can be used to ensure a firm orthogonal mounting angle between each secured flow microscope and a mounting strap may be used to gang two or more flow microscopes together. FIG. 7 depicts another aligned ganging arrangement providing more alignment stability that the arrangement of FIG. 6. Other mounting, ganging, aligning, and fastener arrangements are of course possible and provided for by the invention. For example, the flow microscopes may be additionally or alternatively attached on other portions of the housing, flow fittings, etc. Resultantly ganged pluralities of flow microscopes can be vertically oriented, horizontal oriented, etc. Additionally, pluralities of ganged flow microscopes can themselves be ganged to create larger or more complex arrays.

Figure 8:
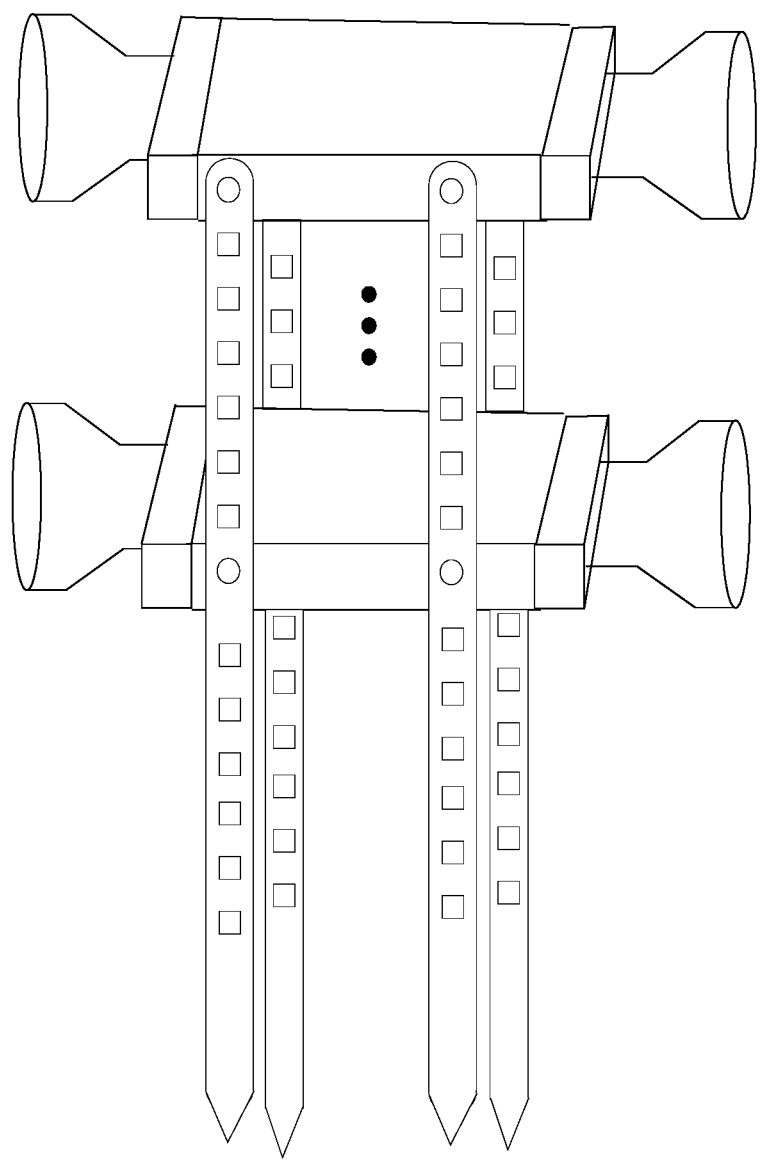
FIG. 8 depicts the exemplary aligned ganging arrangement of FIG. 7 adapted to provide staking as can be used to secure a flow camera in a surface waterway or body of water.

Such ganged pluralities of flow microscopes can be secured to the water floor or shoring in various ways. As one example, the ganging arrangements of FIG. 6 FIG. 7, etc. may be combined with a staking arrangement (for example, those depicted in any of FIGS. 5a-5d) on one of the flow microscopes. Alternatively, FIG. 8 depicts the aligned ganging arrangement of FIG. 7 adapted to provide staking as can be used to secure a flow camera in a surface waterway or body of water. Other arrangements are of course also possible and provided for by the invention.

Figure 9:
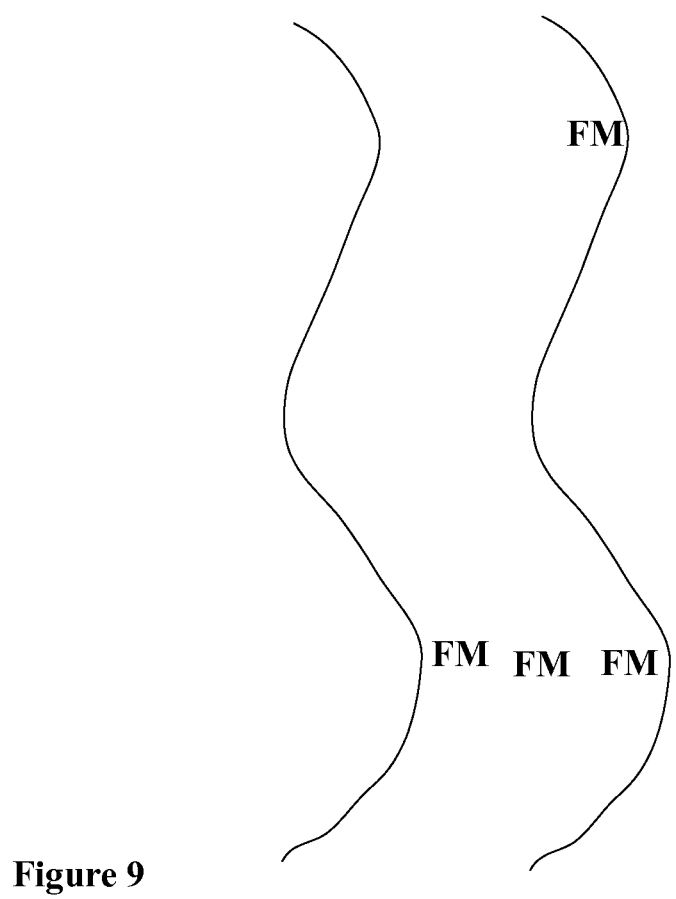
FIG. 9 depicts exemplary locations where one or more flow cameras may be located in a flowing waterway.

FIG. 9 depicts locations in a flowing waterway where one or more flow microscopes can be located in the manner described above.

Exemplary Embodiments for Bioreactor Monitoring Applications

Figure 10:
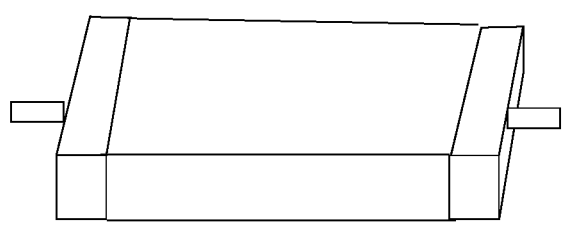
FIG. 10 depicts an exemplary housing arrangement for the exemplary embodiment of FIG. 1b.

As another application setting, the invention can be used in bioreactor process monitoring. FIG. 10 depicts a housing arrangement for FIG. 1*b*. As described earlier, the invention can include valves, pumps, and additional sensors (such as oxygen sensor, carbon dioxide sensor, pH sensor, temperature sensor, specialized ion sensor, affinity sensor, biomolecule sensor, etc.) as can be advantageous in a product or an application.

Figure 11:
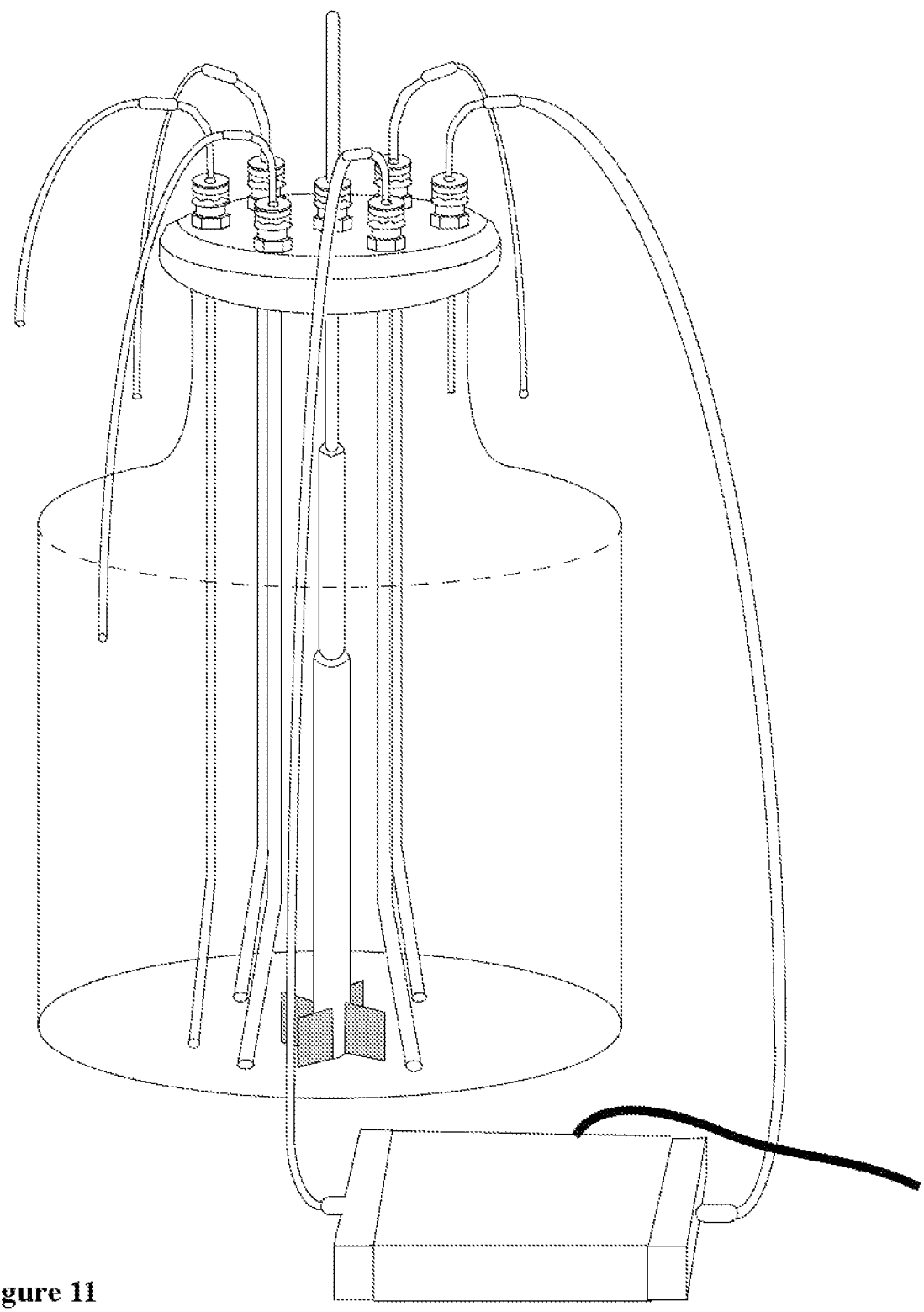
FIG. 11 depicts an exemplary application of the arrangement depicted in FIG. 10 in use with a laboratory or industrial bioreactor.

FIG. 11 depicts an application of the arrangement depicted in FIG. 10 for use with a laboratory or industrial bioreactor. In such an arrangement, it is likely advantageous for the flow microscope to include at least one pump so as to circulate the fluid out from and back into the bioreactor vessel. Such an arrangement may be useful for monitoring the density, development, health, activity, etc of micro-organism populations within the fluid in the bioreactor vessel.

Other Applications

The invention can also be used in a wide range of other applications, such as monitoring in manufacturing processes or monitoring body fluids in medical applications.

It is also noted that the imaging systems about to be described provide a platform for various types of optical microscopic tomography. This opens a very wide set of new possibilities and applications in the areas of microbiology, micro-fabrication, etc.

Exemplary Microscopic Imaging Implementations

The invention provides for small-sized, inexpensive, and innovative electronic imaging arrangements used to provide imaging functions for the flow microscope. A lens-based optical imaging system can be employed typically this would adding to cost, complexity, and size of the device. Alternatively, as discussed below, imaging sensing can be implemented without lenses in a 2-dimensional manner similar to the 1-dimensional imaging arrangements of a document scanner. In these approaches, effectively each image sensor pixel captures immediately emerging light from the fluid or its contents as will be explained. The various arrangements that can be used to leverage and exploit this optical arrangement can also be used to provide a platform for various types of optical microscopic tomography.

To begin, attention is first directed to a representative sample of the state of the art in high-resolution image sensor elements and comparing the direct-contact pixel count and spatial distribution to imaging of some representative one-celled organisms that would be of interest in monitoring environmental water conditions.

FIG. 12*a* is a table comparing attributes example contemporary high-resolution optical image-sensing element products to the width of example Amoeba sizes. Each row in the table represents an example commercial image sensor product whose resolution (indicated in column 5) ranges from 786,432 pixels to 11.1 million pixels. The spatial distribution of the pixels for each product is compared to the size of larger type of Amoeba, ranging from 700 micro-meters to 1000 micro-meters. The 6th and 7th column of the table represent how many pixels would be sufficient to cover the physical area of the size of one Amoeba.

FIG. 12*b* is a table comparing attributes example contemporary high-resolution optical image-sensing element products to the width of example Protozoa sizes. This table is similar but directed to various sizes of Protozoa, which typically ranges from 10 to 1000 micro-meters. The 6th, 7th, and 8th column of the table represent how many pixels would be sufficient to cover the physical area of the size of one Protozoa.

FIG. 12*c* is a table comparing attributes example contemporary high-resolution optical image-sensing element products to the width of example Rotifer sizes. The size of one type of Rotifier typically ranges 100 to 500 micro-meters, and that of another type ranges from 50 to 2000 micrometers. The 6th, 7th, and 8th columns of the table represent how many pixels would be sufficient to cover the physical area of the size of one Rotifier.

In summary, the current state of the art in image sensor products can produce "direct contact" images that would display at the following sizes on contemporary computer monitors:

Protozoa 10 µm in size
    Andanta Ultra-High Res CCD with 11.1 mega-pixel
        13.05 mm (0.51") on a Windows system
        17.40 mm (0.69") on an Apple/Macintosh system
    Megaplus ER 11000 with 96 mega-pixel
        293.99 mm (11.57") on a Windows system
        391.98 mm (15.43") on an Apple/Macintosh system
Amoeba 700 µm in size
    Andanta Ultra-High Res CCD with 11.1 mega-pixel
        913.66 mm (35.97") on a Windows system
        1218.19 mm (47.96") on an Apple/Macintosh system
    Megaplus ER 11000 with 96 mega-pixel
        20579.34 mm (810.21") on a Windows system
        27438.46 mm (1080.25") on an Apple/Macintosh system
Rotifiers 2000 µm in size
    Andanta Ultra-High Res CCD with 11.1 mega-pixel
        2610.46 mm (103") on a Windows system
        3480.53 mm (137") on an Apple/Macintosh system
    Megaplus ER 11000 with 96 mega-pixel
        58798.12 mm (2315") on a Windows system
        78395.61 mm (3086") on an Apple/Macintosh system The above calculations are based on Microsoft Windows operating system default display "DPI" of 96 PPI (one pixel occupies 0.2646 millimeters on the display screen) and Apple/Macintosh default of 72 PPI (one pixel occupies 0.3528 millimeters on the display screen).

Thus contemporary image sensors provide adequate resolution to provide usable 2-dimensional contact imaging at the scale of microorganisms of interest.

Additionally it is noted that the resolution and pixel-count of electronic image sensors (CCD, CMOS, photodiode, etc.) continues to improve annually, increasing the number of pixels that can be used to directly observe such microscopic organisms. On the contrary, some of the image sensors of older digital cameras of lower resolution are found to be insufficient. FIG. 13 is a table comparing attributes example contemporary miniature inexpensive cell-phone camera image-sensing element products to the width of example Amoeba sizes. The 6th and 7th column of the table represent how many pixels would be sufficient to cover the physical area of the size of one Amoeba, and such numbers are significantly lower than the models of camera discussed in earlier tables.

Figure 14A:
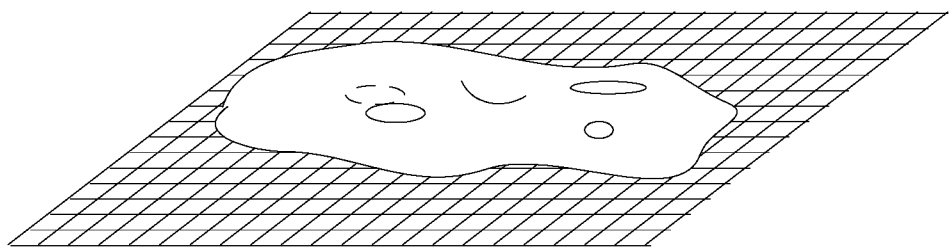
FIG. 14a depicts an exemplary single-cell organism in comparison with an exemplary image sensor pixel array spacing.
Figure 14B:
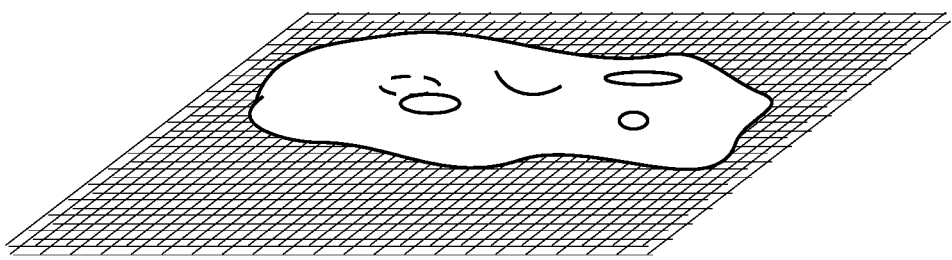
Figure 14C:

Further as to the use of contemporary image sensors for 2-dimensional contact imaging at the scale of microorganisms of interest, for the sake of illustration FIG. 14*a* depicts an exemplary single-cell organism in comparison an exemplary image sensor pixel array spacing, while FIG. 14*b* depicts the exemplary single-cell organism in comparison an exemplary image sensor pixel array spacing of twice the resolution and FIG. 14c depicts the exemplary single-cell organism in comparison an exemplary image sensor pixel array spacing of four times the resolution.

Figure 15:
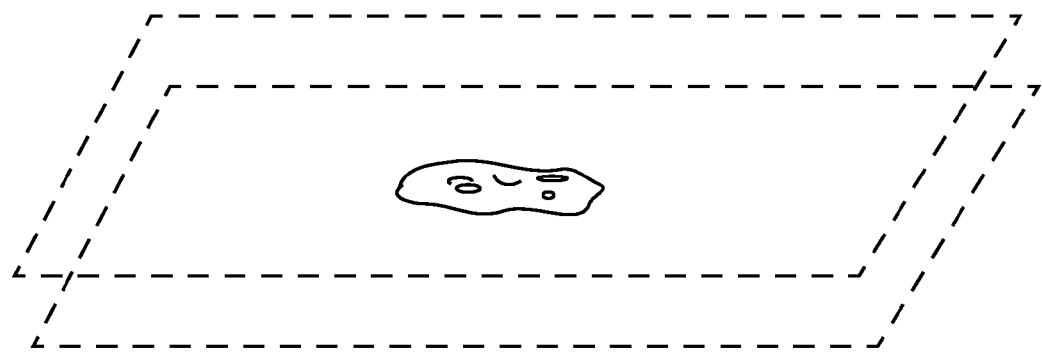
FIG. 15 depicts an exemplary single-cell organism in a fluid region between a planar illumination surface (top) and a parallel planar image sensing surface (bottom).

Attention is now directed to FIG. 15 which depicts an exemplary single-cell organism in a fluid region between a planar illumination surface (top) and a parallel planar image sensing surface (bottom). The planar illumination surface may be a uniformly lit optically diffused light source, a structured collimated light source, etc.

Figure 16:
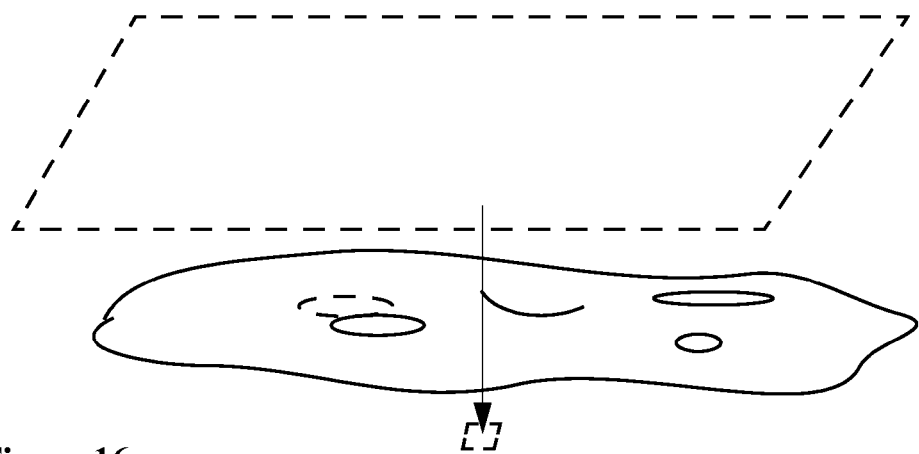
FIG. 16 depicts an exemplary straight light path through an exemplary translucent single-cell organism in a fluid region from an exemplary first area of the planar illumination surface to an exemplary pixel in the image sensor.
Figure 17:
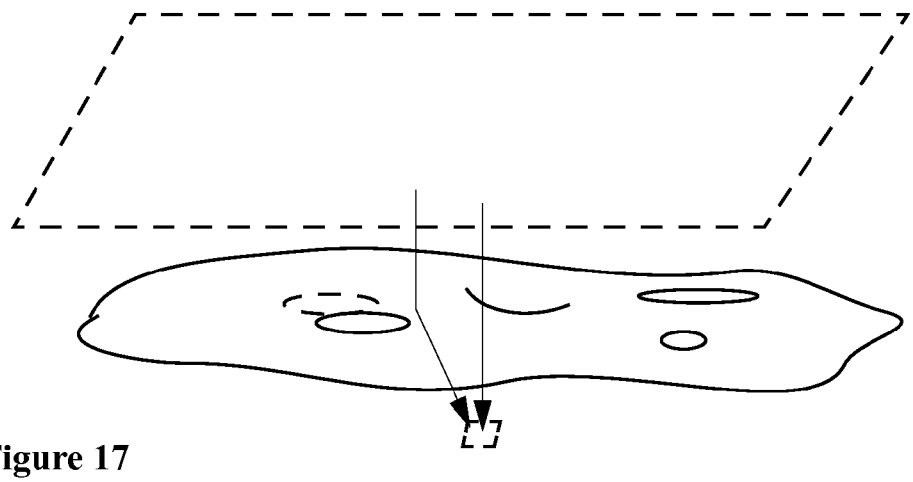
FIG. 17 depicts an augmentation of FIG. 16 also including an exemplary bent light path through an exemplary translucent single-cell organism in a fluid region from an exemplary second area of the planar illumination surface to an exemplary pixel in the image sensor.

FIG. 16 depicts an exemplary straight light path through an exemplary translucent single-cell organism in a fluid region from a first area of the planar illumination surface to a pixel in the image sensor. Such a light path would be produced by either a collimated or a optically diffused light source. As a next step, FIG. 17 depicts an augmentation of FIG. 16 which also includes a bent light path through the translucent single-cell organism in a fluid region from an second area of the planar illumination surface to a pixel in the image sensor. The image sensor pixel received the sum of both light paths, thus contributing to a lack of sharpness of the captured image and potentially other effects. It is noted that there is a huge distribution of such bent light paths, even with a collimated light source.

Figure 18:
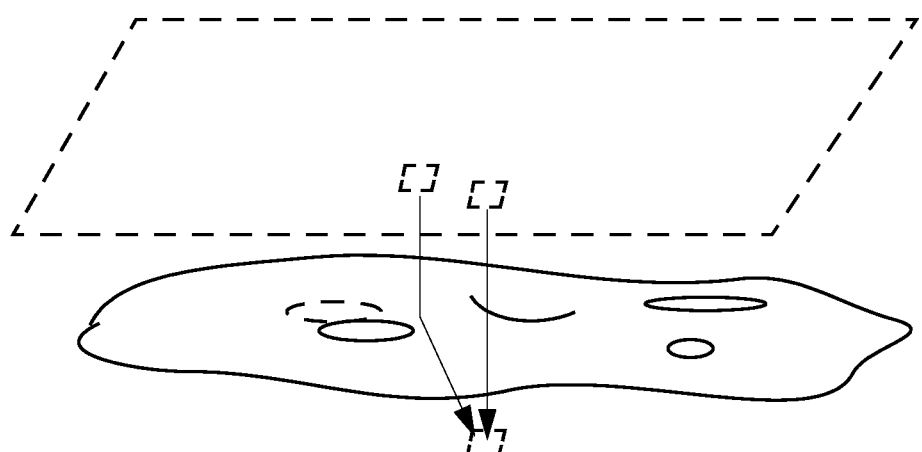
FIG. 18 depicts an adaptation of the situation depicted in FIG. 17 wherein the planar illumination surface comprises individual light-emitting pixels, one which serves as the exemplary first area of the planar illumination surface and the other of which serves as the exemplary second area of the planar illumination surface.
Figure 19:
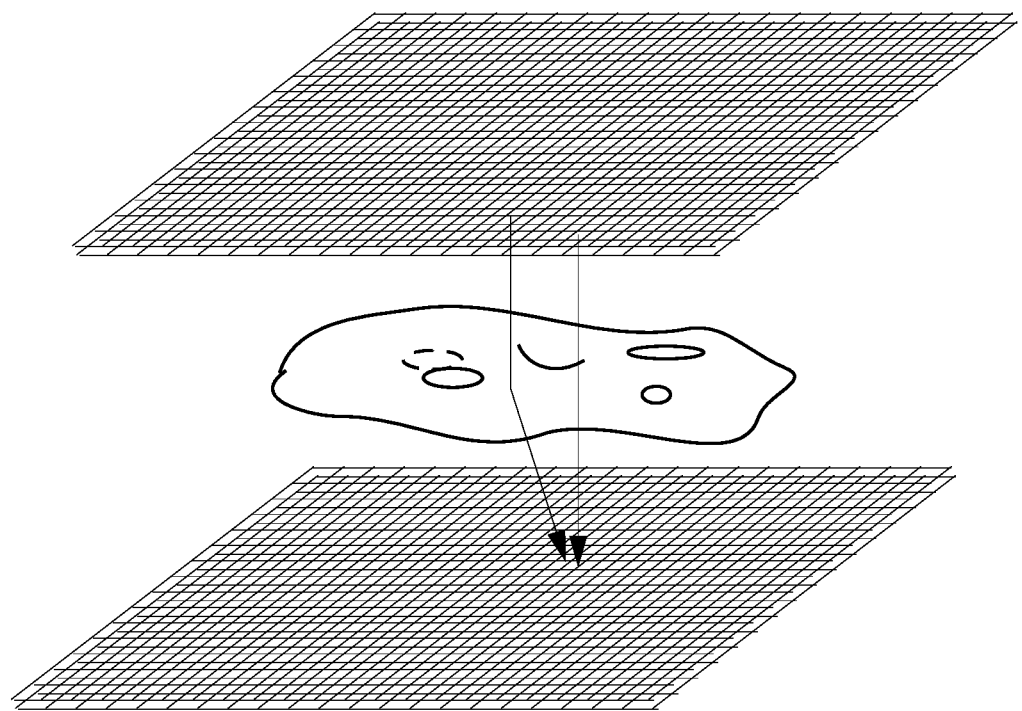
FIG. 19 depicts a larger scale view of the situation depicted in FIG. 18 wherein the planar illumination surface is an array of light-emitting elements and areas of both the planar illumination array and the image sensor array are depicted.

To address this, FIG. 18 depicts an adaptation of the situation depicted in FIG. 17 wherein the planar illumination surface comprises individual light-emitting pixels, one which serves as the first area of the planar illumination surface and the other of which serves as the second area of the planar illumination surface. Such a pixilated light-emitting planar illumination surface, if configured so that each light-emitting pixel could be sequenced on and off independently, can be used to create sequenced interpretation of the light measured at the image sensing pixel, distinguishing a straight light path from each of the many possible bent light paths. (It is noted that some light from the straight light path may diffuse, reflect, and/or refract within or from various constituents of the micro-organism or microscopic object and still end up incident on the same image sensing pixel as the straight path does). FIG. 19 depicts a larger scale view of the situation depicted in FIG. 18 wherein the planar illumination surface is an array of light-emitting elements and areas of both the planar illumination array and the image sensor array are depicted. The high-density array of light-emitting elements may comprise light-emitting diodes (LEDs), thin-film/printed organic light-emitting diodes (OLEDs), thin-film/printed organic light-emitting transistors (OLETs), etc. In various implementations the resolutions and spatial layout of the array of light-emitting elements may match, exceed, or be less than that of the image sensor pixel array as may be advantageous for reasons of function, cost, performance, etc. Further, the high-density array of light-emitting elements may comprise light-emitting elements of various wavelengths as may be advantageous in producing traditional optical color images and/or special scientific images. For example, should the microorganisms be provided with fluorescent markers prior to or within the flow microscope, ultraviolet wavelengths can be included (noting that ultraviolet LEDs are currently commercially available from manufacturers such as SET Inc., Photon Systems, etc.).

It is also noted that LEDs behave as (wavelength sensitive) photodiodes. Thus, an LED array can be used as an image sensing array. Additionally, individual elements in an LED array can be switched between idle mode, light-emitting mode, and light sensing mode. Such an arrangement, if used as an image sensor, can be sequentially operated to produce reflected-light contact imaging. In an implementation, the illuminating LED array is used both as a sequentially scanned light source and, via sequencing and/or multiplexing, as a reflective-imaging light sensor.

The parallel surfaces depicted in FIG. 15 (and carrying through in subsequent discussion) are LED arrays.

Figure 20:
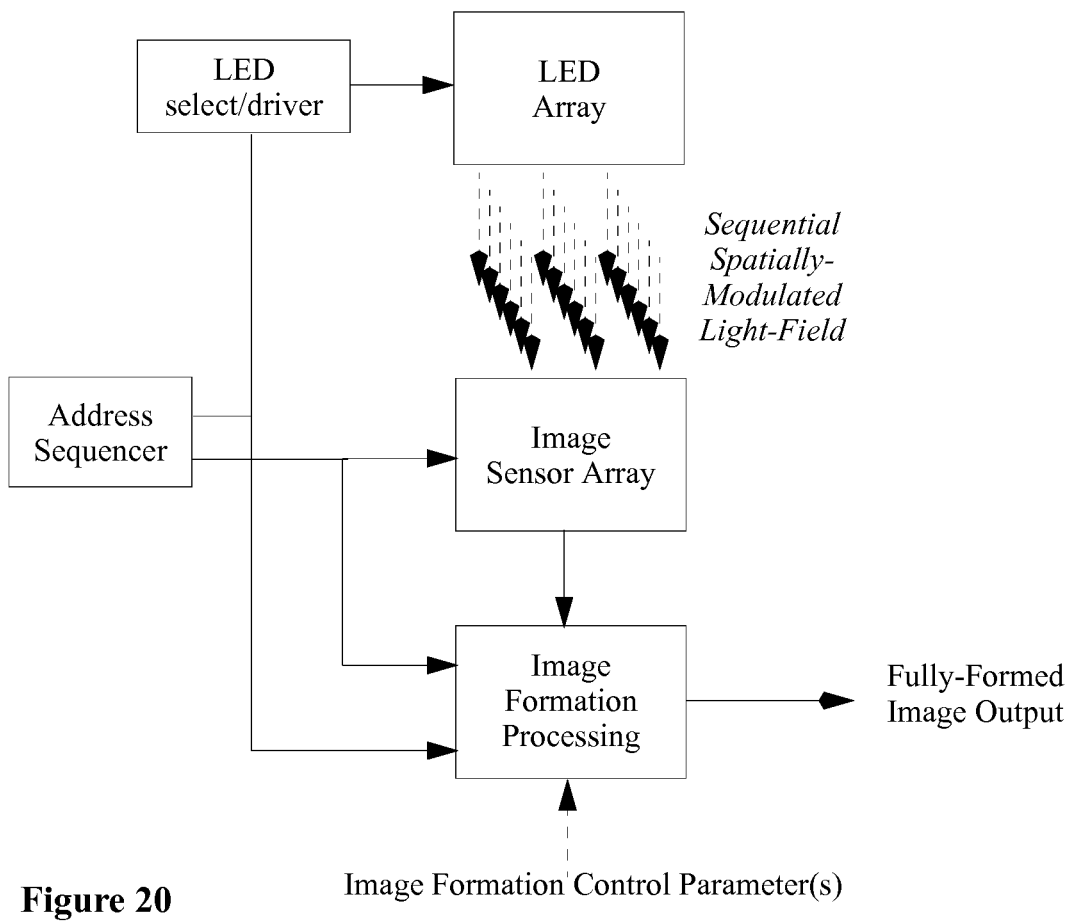
FIG. 20 depicts an exemplary embodiment of a synthetic image formation system employing the optical arrangement depicted in FIG. 19, the embodiment providing a fully-formed image output.
Figure 21:
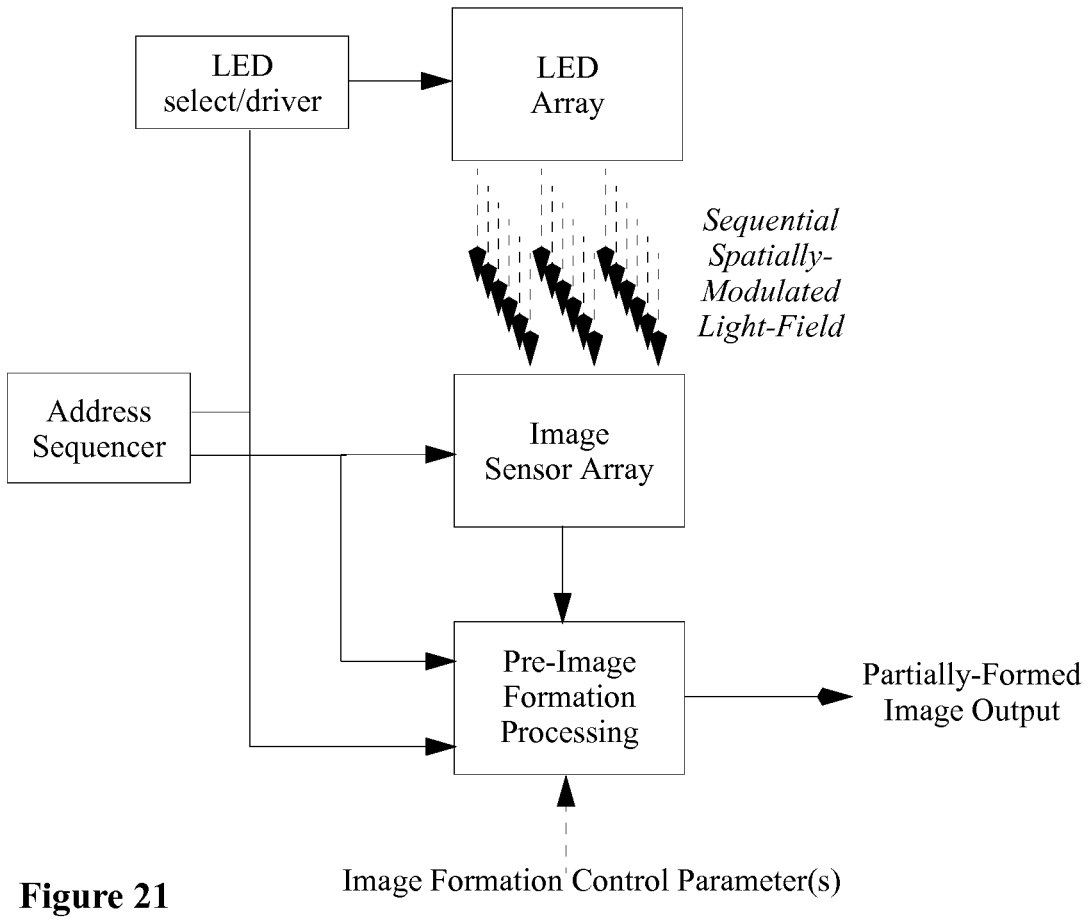
FIG. 21 depicts an exemplary embodiment of a synthetic image formation system employing the optical arrangement depicted in FIG. 19, the embodiment providing a partially-formed image output.
Figure 22:
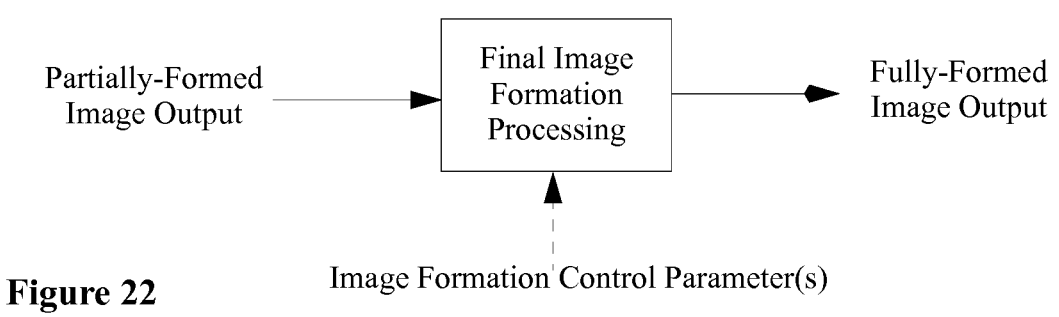
FIG. 22 depicts an exemplary arrangement wherein the partially-formed image output provided by an embodiment such as the exemplary depicted in FIG. 21 is further processed in a subsequent processing step by another processor so as to provide a fully-formed image output.

Referring to the arrangements described in at least terms of FIGS. 20-22, of particular interest is that by combining the temporal sequencing of individual light-emitting pixels with measurements at the optical sensor, the arrangements described above provide:

A means for obtaining a reasonably clear "traditional" optical transmission microscope type of image; and, even more interestingly The data measurement framework with which to implement various types of computed optical tomography.

The first-listed item well-serves the aforementioned applications in environmental science and bioreactor monitoring. The second-list item, i.e. the ability to perform a range of various types of computed optical tomography, provides a wide range of additional potential applications.

FIG. 20 depicts a synthetic image formation system employing the optical arrangement depicted in FIG. 19. In principle the arrangement may be used for traditional optical transmission microscope imaging as well as at least some forms of computed tomography imaging. This arrangement provides a fully-formed image output. Depending on the performance of various components, the system can produce individual or sequences of still images or live video-rate image streams.

Alternatively, FIG. 21 depicts a synthetic image formation system employing the optical arrangement of FIG. 19, and provides a partially-formed image output. FIG. 22 depicts an arrangement wherein the partially-formed image output provided is further processed in a subsequent processing step of another processor to provide a fully-formed image output.

Exemplary Electronic, Signal, and Power Implementations

Figure 23:
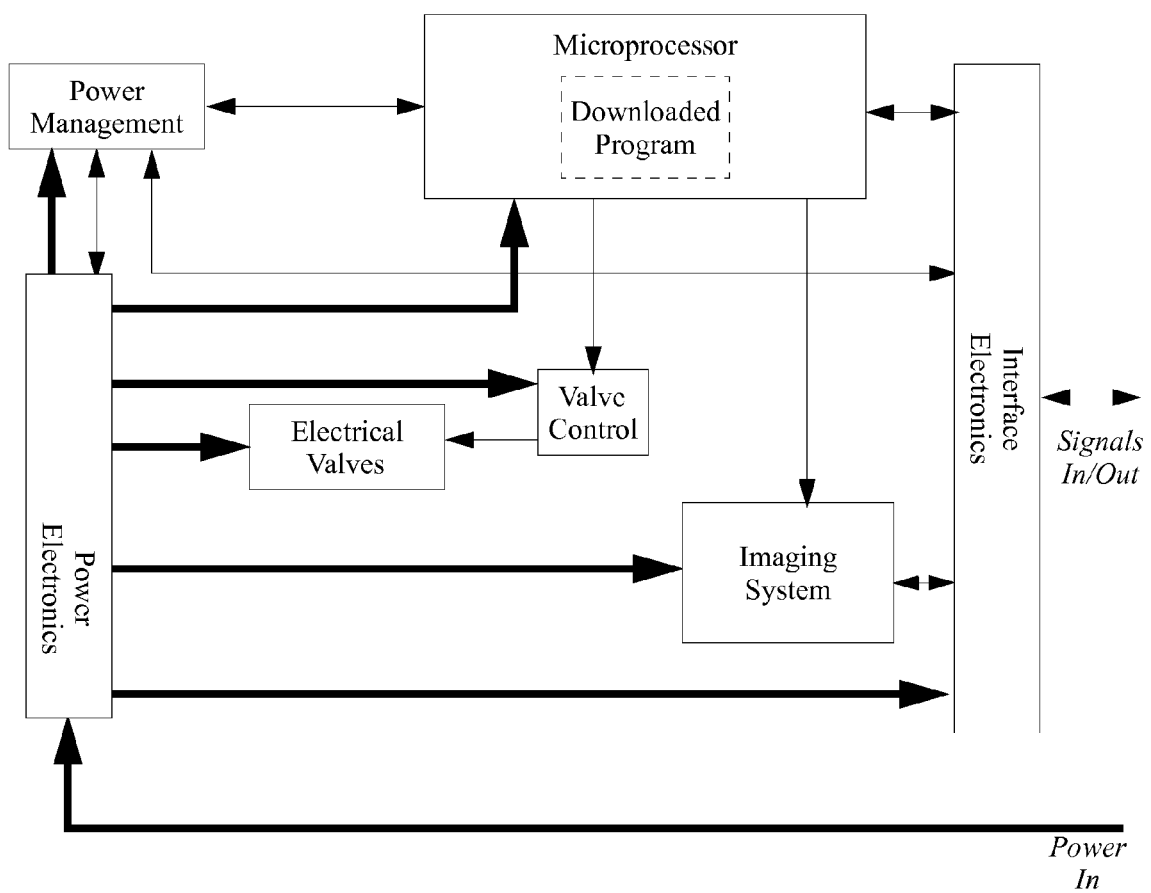
FIG. 23 depicts an exemplary embodiment of the internal elements, signal flows, and power flows for the invention.

FIG. 23 depicts the internal elements, signal flows, and power flows for the invention. Particularly in deployed environmental monitoring situations, power usage and management can be critical. Valves may be impulse-actuated or motor-actuated (rather than constant-duty solenoid) to limit power consumption.

In a deployment, solar power may be used to charge batteries or high-Faraday capacitors for use in power management for the flow microscope and/or associated technologies such as telemetry transmitters, transceivers, transponders, recording devices, beacons, associated sensor devices, etc.

A vane or turbine pump in the observed fluid flow path in the flow microscope device may be used as a generator for energy harvesting from water current flows through the device.

A parallel flow path through the flow microscope device may be used to operate a dedicated electrical generator for energy harvesting from water current flows through the device.

Figure 24:
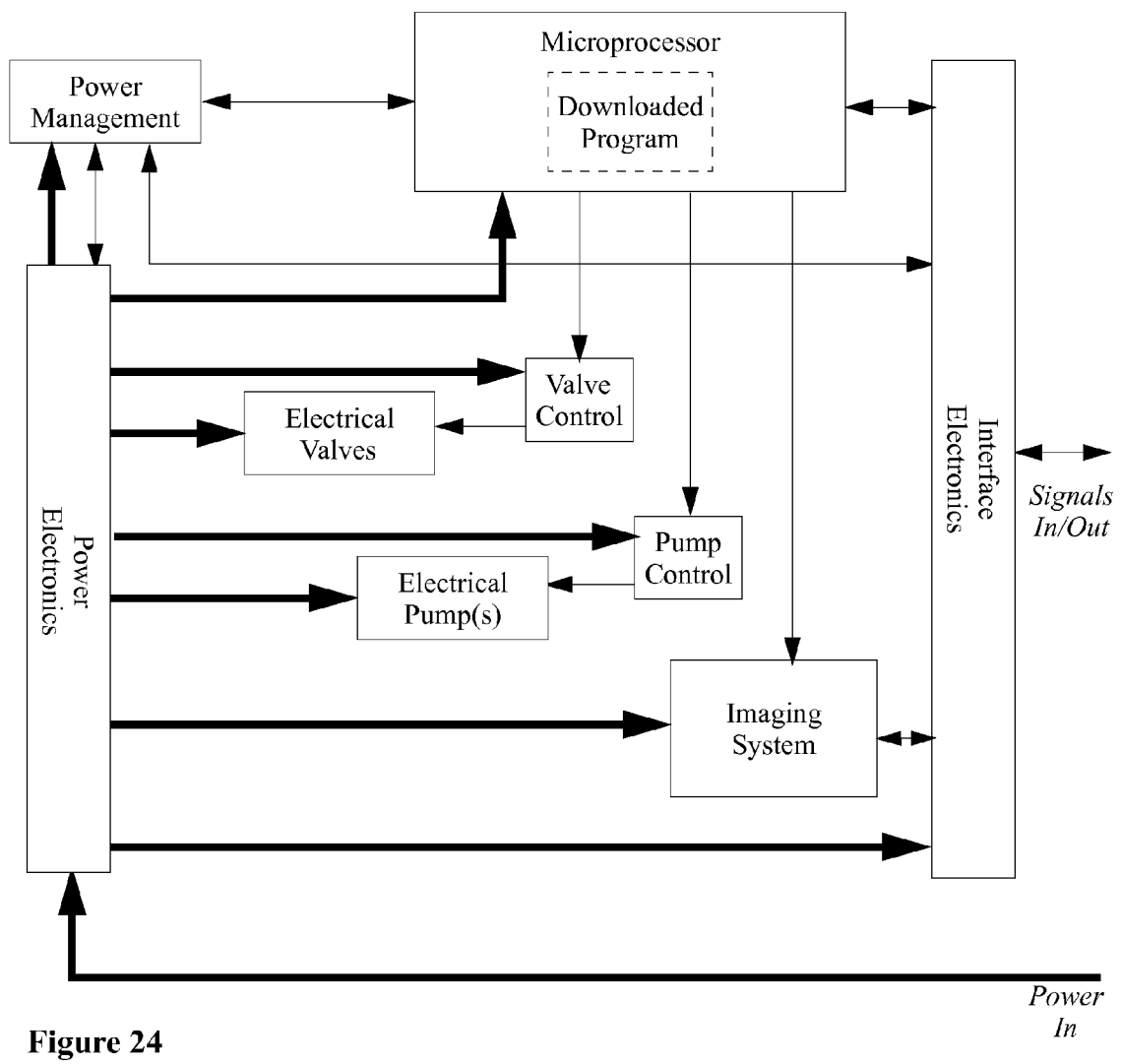
FIG. 24 depicts an augmentation to that depicted in FIG. 23 wherein controlled pumps are added.
Figure 25:
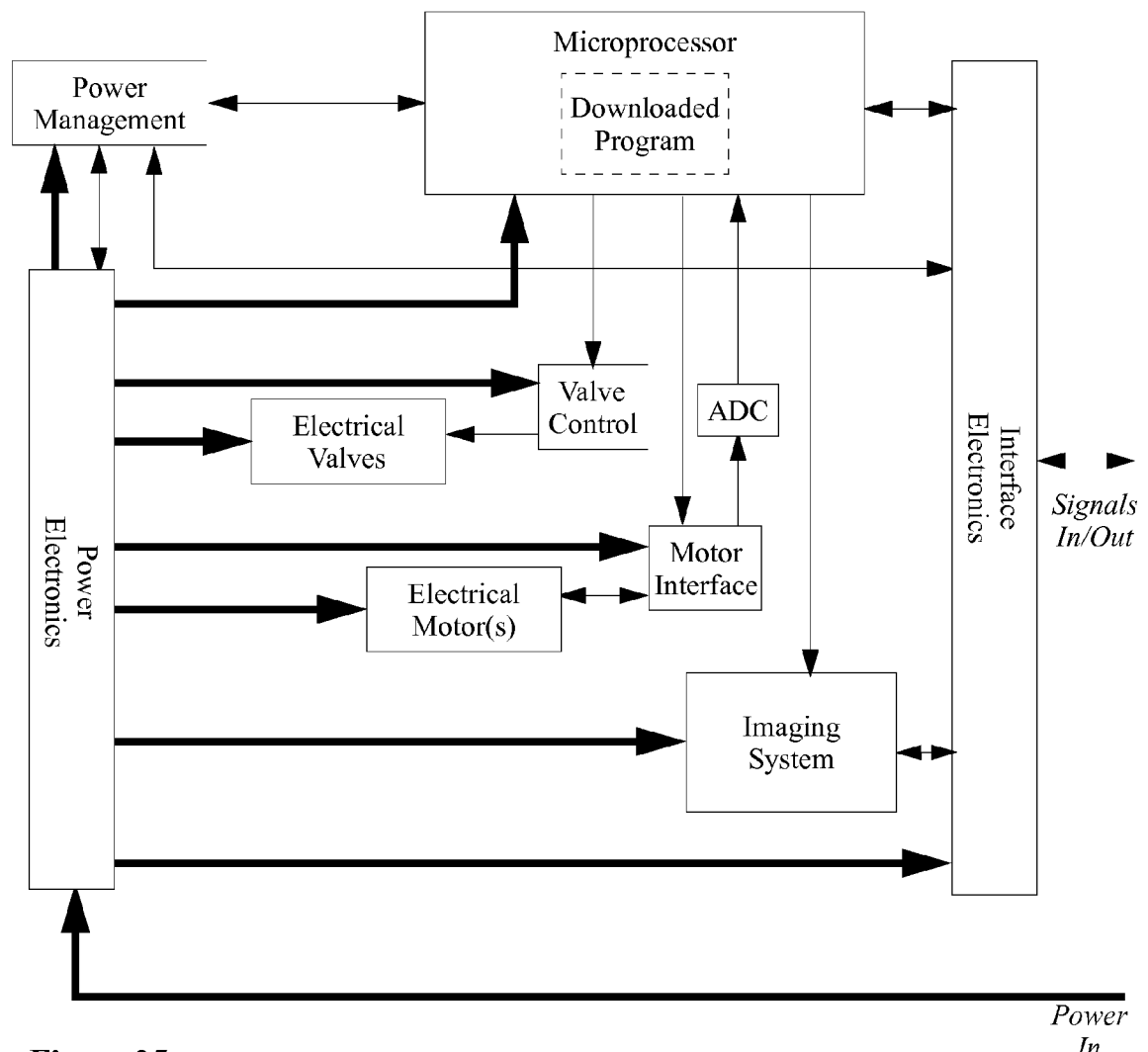
FIG. 25 depicts an augmentation to that depicted in FIG. 23 wherein controlled motors are added and analog signals relating to motor operation are processed by an Analog-to-Digital converter and forwarded to the microprocessor.
Figure 26:
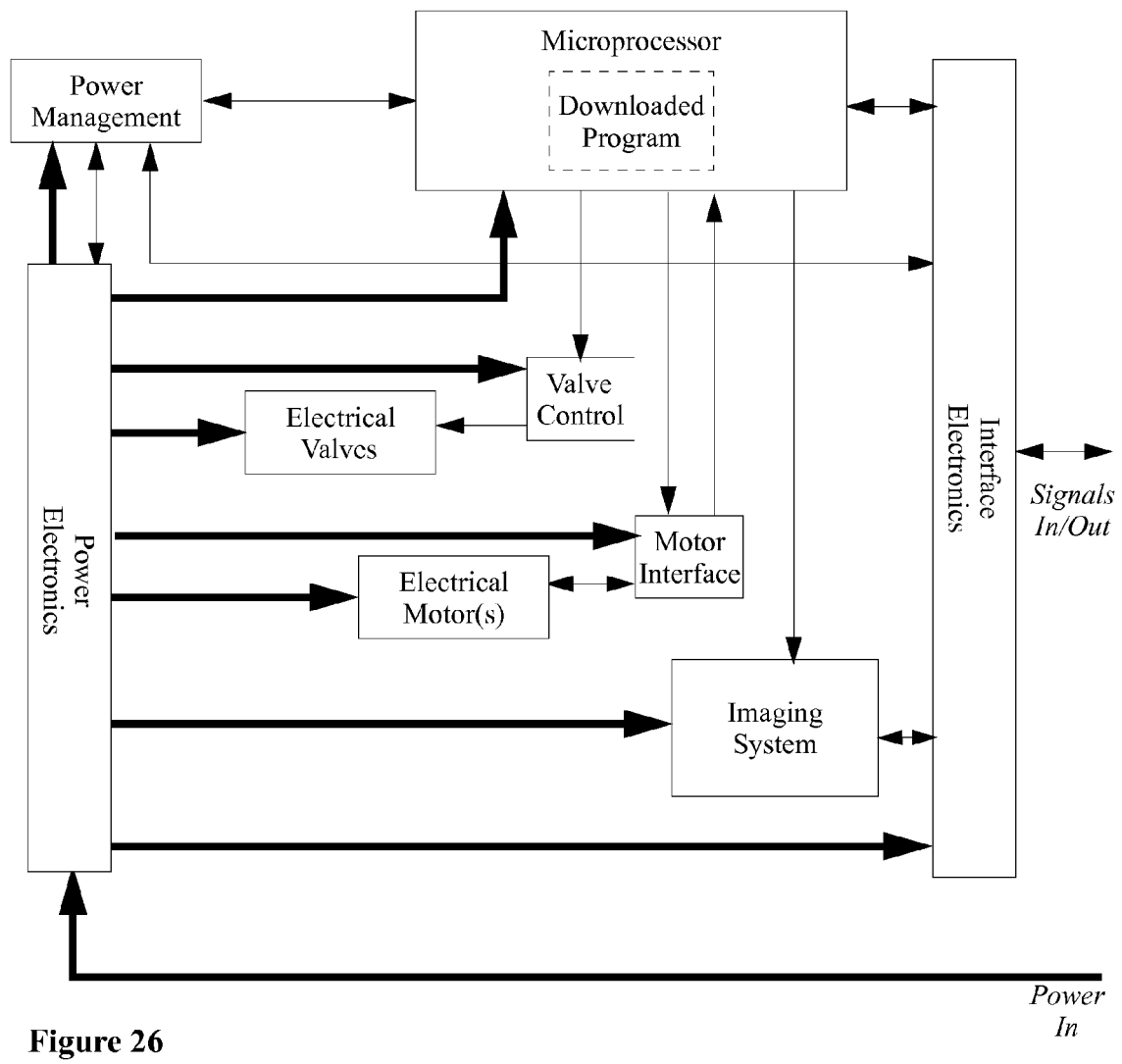
FIG. 26 depicts an augmentation to that depicted in FIG. 23 wherein controlled motors are added and signals relating to motor operation are directly forwarded to the microprocessor; depending on implementation, the signals relating to motor operation may be analog, digital, or both.

FIG. 24 depicts an augmentation to that depicted in FIG. 23 wherein controlled pumps are added. FIG. 25 depicts an augmentation to that depicted in FIG. 23 wherein controlled motors are added and analog signals relating to motor operation are processed by an Analog-to-Digital converter and forwarded to the microprocessor. Each such motor can be a pump motor. Such a pump motor can be monitored during motor operation (for example, monitoring measured operating current) or during idle operation (to serve as a flow meter) and/or in power harvesting motor (to monitor energy generated). FIG. 26 depicts an augmentation to that depicted in FIG. 23 wherein controlled motors are added and signals relating to motor operation are directly forwarded to the microprocessor; depending on implementation, the signals relating to motor operation may be analog, digital, or both. Should the signals be analog, the microprocessor may be of a mixed-signal type (such as a low-power 8051 mixed-signal microprocessor). Examples of digital signal that could be provided include rotation counters, temperature sensor chips, etc.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. Therefore, the invention properly is to be construed with reference to the claims.

I claim:

1. A flow microscope for imaging objects in fluid flows, the flow microscope comprising:
   a fluid conduit comprising a port on each end of a thin flat transparent fluid transport region, the transparent fluid transport region comprising two parallel flat sides;
   a planar illumination surface in physical contact with one of the flat sides of the transparent fluid transport region; and
   a planar image sensing surface in physical contact with the other of the flat sides of the transparent fluid transport region, the planar image sensing surface receiving light fields from the planar illumination surface and responsively creating electrical image signals;
   wherein light from the planar illumination surface travels into the transparent fluid transport region, producing a resulting light field affected by fluid in the fluid conduit and any objects in the fluid,
   wherein the resulting light field is presented to the planar image sensing surface, and
   wherein the planar image sensing surface creates electrical image signals responsive to the resulting light field.

2. The flow microscope of claim 1 wherein the planar illumination surface is electrically powered.

3. The flow microscope of claim 1 wherein the planar illumination surface comprises an array of light-emitting elements.

4. The flow microscope of claim 1 wherein the planar illumination surface comprises an array of light-emitting diodes (LEDs).

5. The flow microscope of claim 1 wherein the planar illumination surface comprises an array of organic LEDs.

6. The flow microscope of claim 1 wherein the planar illumination surface comprises an array of organic LEDs (OLETs).

7. The flow microscope of claim 3 wherein a light-emitting element in the array of light-emitting elements also serves as a light sensor.

8. The flow microscope of claim 7 wherein the array of light-emitting elements also serves as an image sensor.

9. The flow microscope of claim 1 wherein the light-emitting elements in the array of light-emitting elements are illuminated sequentially.

10. The flow microscope of claim 9 wherein the sequential illumination of the light-emitting elements in the array of light-emitting elements is used in image formation.

11. The flow microscope of claim 10 wherein the image formation produces a fully-formed image output.

12. The flow microscope of claim 10 wherein the image formation produces a partially-formed image output.

13. The flow microscope of claim 12 wherein the partially-formed image output is subsequently processed by a processor to produce a fully-formed image output.

14. The flow microscope of claim 10 wherein the image formation produces an output that can be used in optical tomography.

15. The flow microscope of claim 1 further comprising at least one valve.

16. The flow microscope of claim 1 further comprising at least one pump.

17. The flow microscope of claim 16 wherein the pump can also be used to generate electrical power.

18. The flow microscope of claim 16 wherein the pump can also be used to measure the rate of fluid flow through the flow microscope.

19. The flow microscope of claim 1 further comprising power management electronics.

20. The flow microscope of claim 1 further comprising at least one additional sensor.

* * * * *